United States Patent [19]

Ichihara et al.

[11] Patent Number: 5,852,000
[45] Date of Patent: *Dec. 22, 1998

[54] CARDIAC REHABILITATION AGENT

[75] Inventors: Kazuo Ichihara, Sapporo; Hiroomi Yokoyama, Tokushima, both of Japan

[73] Assignee: Otsuka Pharmaceutical Factory, Inc., Tokushima, Japan

[*] Notice: This patent issued on a continued prosecution application filed under 37 CFR 1.53(d), and is subject to the twenty year patent term provisions of 35 U.S.C. 154(a)(2).

[21] Appl. No.: 665,505

[22] Filed: Jun. 18, 1996

Related U.S. Application Data

[63] Continuation of Ser. No. 416,850, Apr. 14, 1995, abandoned.

[30] Foreign Application Priority Data

Aug. 25, 1993 [JP] Japan .................................... 5-210096

[51] Int. Cl.$^6$ ................................................ A61K 31/70
[52] U.S. Cl. ................................ 514/45; 514/46; 514/47; 514/49; 514/50; 514/51
[58] Field of Search ................................ 514/45, 46, 47, 514/49, 50, 51

[56] References Cited

U.S. PATENT DOCUMENTS

| | | | |
|---|---|---|---|
| 4,693,995 | 9/1987 | Prino et al. | 514/44 |
| 4,758,553 | 7/1988 | Ogoshi | 514/47 |
| 4,880,783 | 11/1989 | Mentzer et al. | 514/46 |
| 5,189,027 | 2/1993 | Miyashita et al. | 514/46 |
| 5,190,948 | 3/1993 | Materazzi et al. | 514/50 |
| 5,470,838 | 11/1995 | von Borstel et al. | 514/50 |

FOREIGN PATENT DOCUMENTS

| | | |
|---|---|---|
| 4242830 | 8/1931 | Japan . |
| 60-188434 | 9/1985 | Japan . |
| 3502694 | 6/1991 | Japan . |
| 59121 | 1/1993 | Japan . |
| 559087 | 3/1993 | Japan . |
| 5163294 | 6/1993 | Japan . |
| 5208993 | 8/1993 | Japan . |

OTHER PUBLICATIONS

JPA 2–282378 (Japan Synthetic Rubber Co., Ltd.), Nov. 19, 1990 (English–Language abstract).

*Primary Examiner*—James O. Wilson
*Attorney, Agent, or Firm*—Sughrue, Mion, Zinn, Macpeak & Seas, PLLC

[57] ABSTRACT

This invention provides a cardiac rehabilitation agent comprising at least one species of the class consisting of purine nucleoside and purine nucleotide, e.g. a composition comprising inosine, cytidine, uridine, a salt of guanosine 5'-monophosphate, and thymidine in a molar ratio of 4:4:3:4:1. The cardiac rehabilitation agent of this invention is characterized by excellent cardiac function-restorative activity and no risk of side effect.

8 Claims, 3 Drawing Sheets

CARDIAC REHABILITATION AGENT

This is a Continuation of application Ser. No. 08/416,850 filed Apr. 14, 1995 now abandoned.

TECHNICAL FIELD

This invention relates to a cardiac rehabilitation agent and more particularly to a novel medicinal composition for restoring cardiac function after mechanical revascularization in the treatment of myocardial infarction.

BACKGROUND ART

Myocardial infarction is a disease in which the coronary blood vessels are constricted or obstructed in varying degrees due to thrombus or embolus formation or by spasm of coronary arteries with the result that the heart muscle undergoes ischemic necrosis. Above all, the clinical condition in which a precipitating, serious coronary artery obstruction causes a sudden ischemia of the myocardium, resulting in serious impairment of myocardial contractility to cause life-threatening arrythmia, is known as acute myocardial infarction.

The prognosis of acute myocardial infarction is dependent on the size of the necrotic lesion and the state of the left ventricular function. Therefore, in order to prevent irreversible necrosis of the ischemic myocardium, mechanical revascularization for securing repatency of the obstructed coronary artery is routinely performed at the earliest possible opportunity these days. However, even if the obstruction is a brief one, short of causing irreversible necrosis of the myocardium, it takes several days for the ischemia-compromised myocardial contractility to restore to its pre-obstruction level. This transitory myocardial contraction disturbance is called "stunning myocardium" and is receiving special attention of late as a cardiac dysfunction following mechanical revascularization. Therefore, it is of great significance for improved prognosis of this disease to prevent or palliate said "stunning" to maintain the myocardium in a functionally wholesome state.

As the drugs found to be effective in this restoration of cardiac function following mechanical revascularization in myocardial infarction, a cluster of β-agonists is already known. However, while these drugs certainly increase myocardial contractility to improve cardiac function, they disturb the energy balance of the myocardium (for example, increases in myocardial energy requirements and myocardial oxygen demand) to adversely affect myocardial metabolism (Br. Heart. J., 42, pp.43–50, 1979: Progr. Cardiovasc, Dis., 19, pp.327–340, 1977).

Meanwhile, digitalis, which is a time-honored cardiotonic, has activity to improve cardiac function without increasing myocardial oxygen demand (Cardiovascular Research, 1983, 17, pp.192–199). However, since digitalis has coronary vasoconstrictive activity (Chest., 63, pp.862–867, 1973: Am. J. Cardiol., 41, pp.88–93, 1978), its potential to further aggravate myocardial hemodynamics has been suggested, thus casting doubts on the rationale of its application.

More recently, as a drug substance claimed to increase the production of adenosine, an endogenous physiologically active substance, and, hence to, be effective in improving cardiac function, 5-amino-4-imidazolecarboxamidoriboside (rAICA) has been reported. However, the activity and efficacy of this drug are not adequate and in view of the elucidation that endogenous adenosine alone is not sufficient to account for the reperfusion disturbance antagonizing mechanism, there is room for development of further new drug substances.

DISCLOSURE OF INVENTION

The object of this invention is to overcome the above-mentioned disadvantages, namely serious side effects and inadequate activity and efficacy of the prior art cardiac rehabilitation agents and accordingly to provide a novel cardiac rehabilitation agent insuring an improved cardiac function restorative effect and, at the same time, presenting no risk of adverse reaction.

The above object has been accomplished by the cardiac rehabilitation agent of this invention which is now described in detail.

Thus, this invention provides a cardiac rehabilitation agent comprising at least one species selected from the class consisting of purine nucleoside (exclusive of adenosine) and purine nucleotide as an active component.

As the active component purine nucleoside, inosine is particularly preferred. As said purine nucleotide, guanosine 5'-monophosphate (hereinafter abbreviated as GMP) is particularly preferred. The GMP can also be used in the form of a pharmacologically acceptable alkali metal salt, e.g. sodium salt, potassium salt, etc., and among them, the disodium salt (GMP-2Na) is particularly desirable in view of its high solubility.

A preferred cardiac rehabilitation agent of this invention comprises inosine and GMP as active components.

Another preferred cardiac rehabilitation agent of this invention contains a pyrimidine nucleoside, such as cytidine and uridine, as an additional active component.

Still another preferred cardiac rehabilitation agent of this invention contains a purine base, such as adenine and hypoxanthine, as an additional active component.

An especially preferred cardiac rehabilitation agent of this invention comprises inosine, cytidine, uridine, GMP (or a salt thereof) and thymidine as active components. The most advantageous is the above composition in which said components occur in a molar ratio of 4:4:3:4:1.

The active component purine nucleoside in the present cardiac rehabilitation agent may be any known purine nucleoside excluding adenosine, thus including inosine, guanosine and so on. These may be used alone or in combination. Among them, inosine is particularly preferred. The active component purine nucleotide may also be any ordinarily known one, including adenylic acid, adenosine triphosphate, guanylic acid (guanosine monophosphate), inosinic acid and so on. These nucleotides may also be used independently or in combination. Of course, said purine nucleoside and purine nucleotide can be used concomitantly as active components.

The cardiac rehabilitation agent of this invention may comprise, in combination, at least one active component selected from among said purine nucleosides (exclusive of adenosine) and purine nucleotides and either a pyrimidine nucleoside or a purine base or both as concomitant active components.

The components that can be concomitantly contained may also be liberally selected from among known compounds, and it is a preferred practice to use two or more different pyrimidine nucleosides from the standpoint of cardiac function restorative effect. The ratio of concomitant pyrimidine nucleoside is not particularly restricted but can be anywhere within the range of generally 0.1–10 molar equivalents and preferably 0.5–2 molar equivalents relative to the purine component (the sum of mols of purine nucleoside, purine nucleotide and purine base).

The cardiac rehabilitation agent of this invention produces an excellent cardiac function restorative effect on the strength of said active components but the desired effect can also be produced by utilizing other nucleic acid components and/or salts thereof in combination with the components mentioned hereinabove. Particularly preferred among other components that can be used in combination is thymidine, the proportion of which can be properly selected within the range of about 0.1–10 mols, preferably 0.1–2 mols, per mol of said purine component. When a compound selected from among said GMP and salts thereof is used as an active component, its proportion can be properly selected from the range of about 0.1–10 molar equivalents, preferably about 0.5–2 molar equivalents, relative to each mol of said purine component.

The formulating amount of said purine base per mol of purine nucleoside and/or purine nucleotide can be properly selected from the range of generally about 0.1–10 molar equivalents and preferably about 0.5–2 molar equivalents.

The preferred typical combinations of the nucleic acid components, inclusive of said purine nucleoside and/or purine nucleotide, which constitute the cardiac rehabilitation agent of this invention are (1) inosine/cytidine, (2) inosine/uridine, (3) guanosine/uridine, (4) guanosine/cytidine, (5) inosine/cytidine/uridine, (6) guanosine/cytidine/uridine, (7) adenosine/inosine/cytidine, (8) adenosine/guanosine/uridine, (9) adenosine/inosine/cytidine/uridine, (10) adenosine/inosine/guanosine/cytidine, (11) cytidine/GMP/uridine/inosine/thymidine, (12) cytidine/GMP-2Na/uridine/inosine/thymidine, (13) cytidine/GMP-2Na/uridine/adenosine/thymidine, (14) cytidine/GMP-2Na/uridine/guanosine/thymidine, (15) adenosine/GMP-2Na/uridine/guanosine/thymidine, and (16) cytidine/adenosine/GMP-2Na/ uridine/inosine/thymidine, among others.

Among the above-mentioned combinations, the combination of (12) cytidine/GMP-2Na/uridine/inosine/ thymidine is particularly preferred and the preferred formulating ratios of the respective members of the combination may typically be 4:4:3:4:1.

The medicinal composition of this invention is prepared by weighing the respective components of the above formulation and processing them into a pharmaceutical preparation suited to the intended use by the established pharmaceutical procedure. The dosage form that can be adopted is not particularly restricted but includes a variety of forms used for ordinary drugs, although an injectable preparation for intravenous administration is particularly preferred. Such injectable preparations can be made available by the per se conventional technology which typically comprises dissolving said respective components together in distilled water for injection, followed where necessary by addition of various conventional additives such as a pH control agent, e.g. hydrochloric acid, acetic acid, malic acid, citric acid, sodium hydroxide or potassium hydroxide, and a stabilizer to provide an aqueous solution generally having a pH of about 6–9, and sterilizing the solution by autoclaving or filtering through a membrane filter. The total concentration of all the active components of the resulting injectable cardiac rehabilitation agent of this invention is not so critical but can generally be about 0.5–10 w/v % and preferably about 2–8 w/v %.

The cardiac rehabilitation agent of this invention, when applied or administered to patients in any of the above-mentioned dosage forms, exerts a potent constrictive action on the myocardium and, yet, offers the advantage of a very low potential of adverse reaction. The dosage for patients cannot be stated in general terms, for it may vary according to the pathological status, age, sex and body weight of each patient, the severity of disease and other factors. Generally, however, an injectable preparation, for one, can be administered in a daily dose of about 0.5–50 ml, preferably about 1–20 ml (about 30–620 mg as active components) for an adult patient as rule of thumb.

BRIEF DESCRIPTION OF DRAWINGS

FIG. 3A is a graph of time (in minutes) plotted against SS%, for the experimental group (i.e., (1)) and the control group treated with saline (i.e., (3)). FIG. 3B is a graph of time (in minutes) plotted against SS %, for the comparison group (i.e., (2)) and the control group treated with saline (i.e., (3)).

BEST MODE FOR CARRYING OUT THE INVENTION

Figure 1:
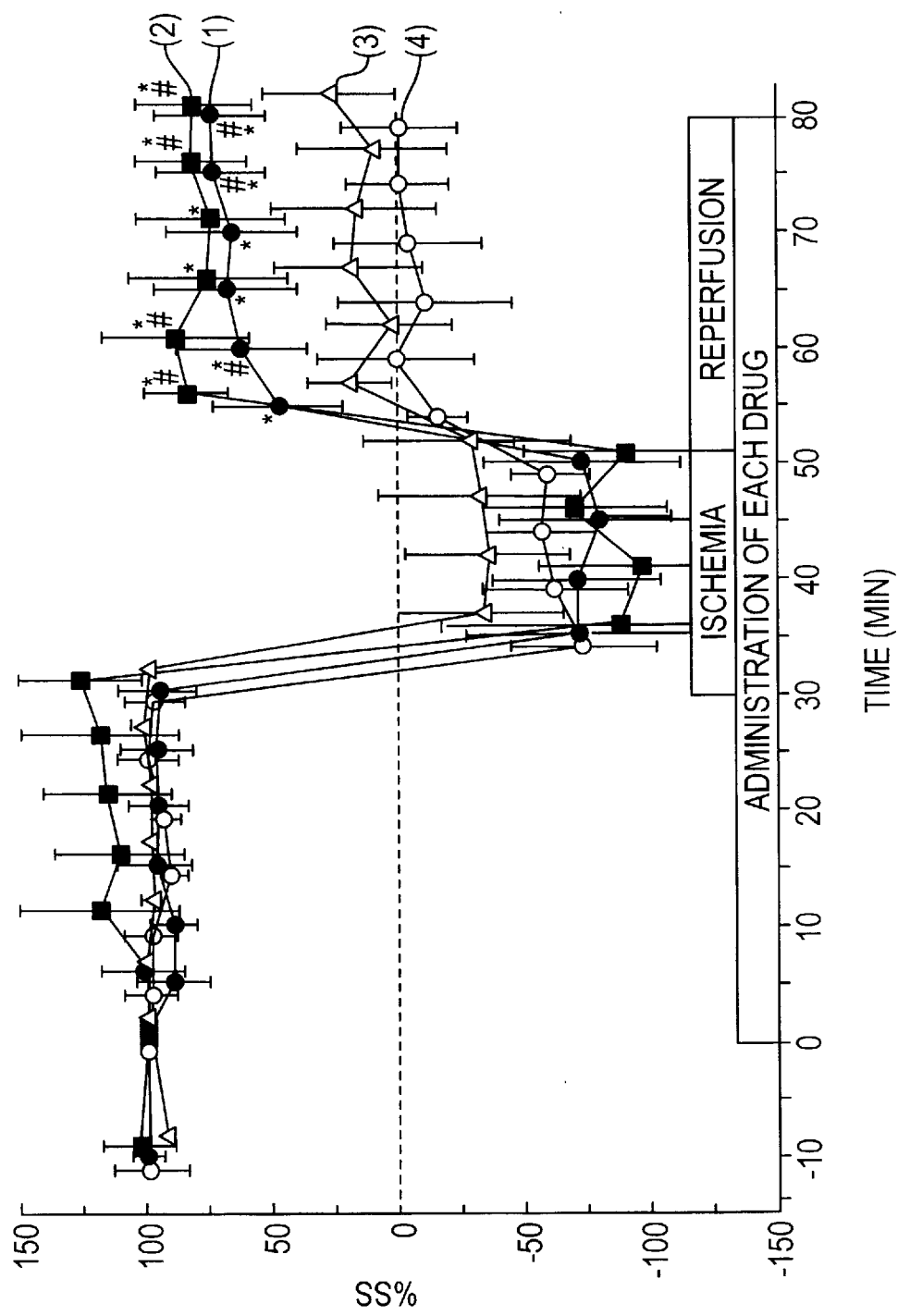
FIG. 1 is a graph showing the post-reperfusion myocardial contractility improving action of the drug of this invention as assayed in Test Example 1 presented hereinafter.

The following examples of production of the drug of this invention as well as pharmacological test examples are intended to describe the invention in further detail.

EXAMPLE 1

Pure crystals of the respective components according to the following formulation (the figure in parentheses denotes the molar ratio) were added to distilled water for injection with stirring to make a total of 1 liter. The aqueous solution thus obtained was filtered through a membrane filter and filled in vials which were then closed. The vials were sterilized by autoclaving at 105° C. for 40 minutes to provide a cardiac rehabilitation drug of this invention in an injectable form (5 ml×200 vials). The total free nucleic acid concentration of this product was 3.35 w/v %.

Inosine 0.80 w/v % (4)
Cytidine 0.73 w/v % (4)
GMP-2Na 1.22 w/v % (4)
Uridine 0.55 w/v % (3)
Thymidine 0.18 w/v % (1)

EXAMPLE 2

Except that the formulation of inosine 30 mM [0.81 w/v % (1)], adenine hydrochloride 30 mM [0.81 w/v % (1)], and uridine 60 mM [1.47 w/v % (2)] was used, the procedure of Example 1 was otherwise repeated to provide a ternary system cardiac rehabilitation drug of this invention.

EXAMPLE 3

Except that the formulation of inosine 53.3 mM [1.43 w/v % (4)], GMP-2Na 53.3 mM [2.17 w/v % (4)] and thymidine 13.3 mM [0.32 w/v % (1)] was used, the procedure of Example 1 was otherwise repeated to provide a ternary system cardiac rehabilitation drug of this invention.

EXAMPLE 4

Except that the formulation of inosine 30 mM [0.81 w/v % (1)] and GMP-2Na 30 mM [1.41 w/v % (1)] was used, the procedure of Example 1 was otherwise repeated to provide a binary system cardiac rehabilitation drug of this invention.

EXAMPLE 5

Using inosine 60 mM (1.62 w/v %) alone, the procedure of Example 1 was otherwise repeated to provide a unitary system cardiac rehabilitation drug of this invention.

EXAMPLE 6

Using GMP-2Na 60 mM (19.7 w/v %), the procedure of Example 1 was otherwise repeated to provide a unitary system cardiac rehabilitation drug of this invention.

Test Example 1

Adult mongrel dogs (4–6 animals per group) were anesthetized with pentobarbital sodium (30 mg/kg, intravenous) and the cardiac rehabilitation drug of Example 1 was administered from the left femoral vein at a rate of 0.1 or 0.2 ml/kg/min over a period of 80 minutes. This group was designated Invention Group 1 (dose 0.1 ml, n=6) or Invention Group 2 (dose 0.2 ml, n=6).

In lieu of the drug of this invention, the same amount of rAICA (30 mM aqueous solution) or saline (0.9% NaCl) was similarly administered to provide Comparison Group (dose of rAICA=0.1 ml, n=4) or Control Group (dose of saline=0.2 ml, n=6).

Thirty (30) minutes after the beginning of administration of each test drug, the animals in the corresponding group were thoracotomized to expose the left ventricular wall and the site about 1 cm from the origin of the left anterior descending coronary artery (LAD) was carefully ablated. Then, a silk suture for coronary artery ligating use was passed on the above site and, at the same time, the probe of an electromagnetic flowmeter was set in position for measurement of coronary blood flow.

Thereafter, an ultrasonic crystal probe was embedded in the left ventricular wall and the length of the myocardium was measured. At the same time, the left ventricular pressure, arterial pressure and heart rate were concurrently monitored. After waiting until the respective parameters had become steady, the coronary artery was completely ligated to maintain the myocardium in an ischemic state for 20 minutes, and this was followed by 30-minute reperfusion.

As indicators of myocardial contractility, measured values of myocardial length and left ventricular pressure were used to calculate the % change in ventricular length (% SS; segment shortening) and left ventricular pressure linear differential (dP/dt).

The results are shown in FIG. 1 (abscissa=time in minutes, ordinate=% SS).

Referring to FIG. 1, (1) represents Invention Group 1 (dose=0.1 ml, n=6), (2) Invention Group 2 (dose=0.2 ml, n=6), (3) Comparison Group (rAICA 0.1 ml, n=4), and (4) Control Group (saline 0.2 ml, n=6). Each datum is mean ± SD. The mark * and mark # stand for p<0.05 (vs. 0.9% NaCl Group) and p<0.05 (vs. rAICA-dosed Comparison Group) according to Tukey's test. The time (min.) was plotted on the abscissa with the point of time of administration of each drug being taken as 0 and any point of time preceding administration being marked with the symbol -. The 30–50-min. period is the ischemic period and the subsequent 50–80-min. period is the reperfusion period.

It is apparent from FIG. 1 that, in the acute myocardial infarction model, post-reperfusion % SS was remarkably improved in the Invention Groups (Invention Groups 1 and 2) as compared with the saline-treated Control Group and rAICA-treated Comparison Group.

The above findings indicate clearly that compared with the Control Group and even with the Comparison Group, the drug of this invention remarkably inhibits stunning myocardium following ischemia-reperfusion without entailing any adverse effect, suggesting that the drug of the invention is very effective for recovery of the myocardium following mechanical revascularization in the treatment of myocardial infarction, thus contributing greatly to improved prognosis.

Test Example 2

From each male Sprague-Dawley rat, the heart was enucleated and promptly mounted in a perfusion equipment and a 5-minute constant-pressure perfusion was performed by the method of Langendorff using Krebs-Henseleit bicarbonate buffer at 37° C. Then, a switch to the working heart technique [Circ. Res., 38, Suppl. 1, 22–30, 1976] was made and a 10-minute perfusion was further carried out. Next, an ischemic heart was constructed by the technique of removing the load on the aortal valve by constructing a bypass [J. Cardiovasc. Pharmacol., 5, 745–751, 1983]. After 40 minutes of ischemia, the afterload was applied again for a 30-minute reperfusion of the heart.

At the above switching to perfusion by the working heart technique, the cardiac rehabilitation agent of Example 1 was added to the perfusion fluid at $\frac{1}{60}$ concentration (2 mM as the total concentration of the components in the perfusion fluid; n=6) (Group 1).

The same test was also performed in (2) a group receiving the cardiac rehabilitation agent of Example 2 at $\frac{1}{60}$ concentration (in the perfusion fluid, inosine 0.5 mM, uridine 1 mM and adenine 0.5 mM, n=6) (Group 2), (3) a group receiving the cardiac rehabilitation agent of Example 3 at $\frac{1}{60}$ concentration (in the perfusion fluid, inosine 0.89 mM, GMP-2Na 0.89 mM, and thymidine 0.22 mM, n=6) (Group 3), (4) a group receiving the cardiac rehabilitation agent of Example 5 at $\frac{1}{60}$ concentration (in the perfusion fluid, inosine 1 mM, n=6) (Group 4), and (5) a group receiving the cardiac rehabilitation agent of Example 6 at $\frac{1}{60}$ concentration (in the perfusion fluid, GMP-2Na 1 mM, n=6) (Group 5). In addition, (6) a control group (n=6, Group 6) receiving the drug-free perfusion fluid only was provided.

The isolated rat hearts in the above groups were respectively perfused by the working heart technique to evaluate the pumping function of the heart.

In this evaluation, the double product, viz. peak systolic pressure × heart rate, was calculated as an indicator.

Figure 2:
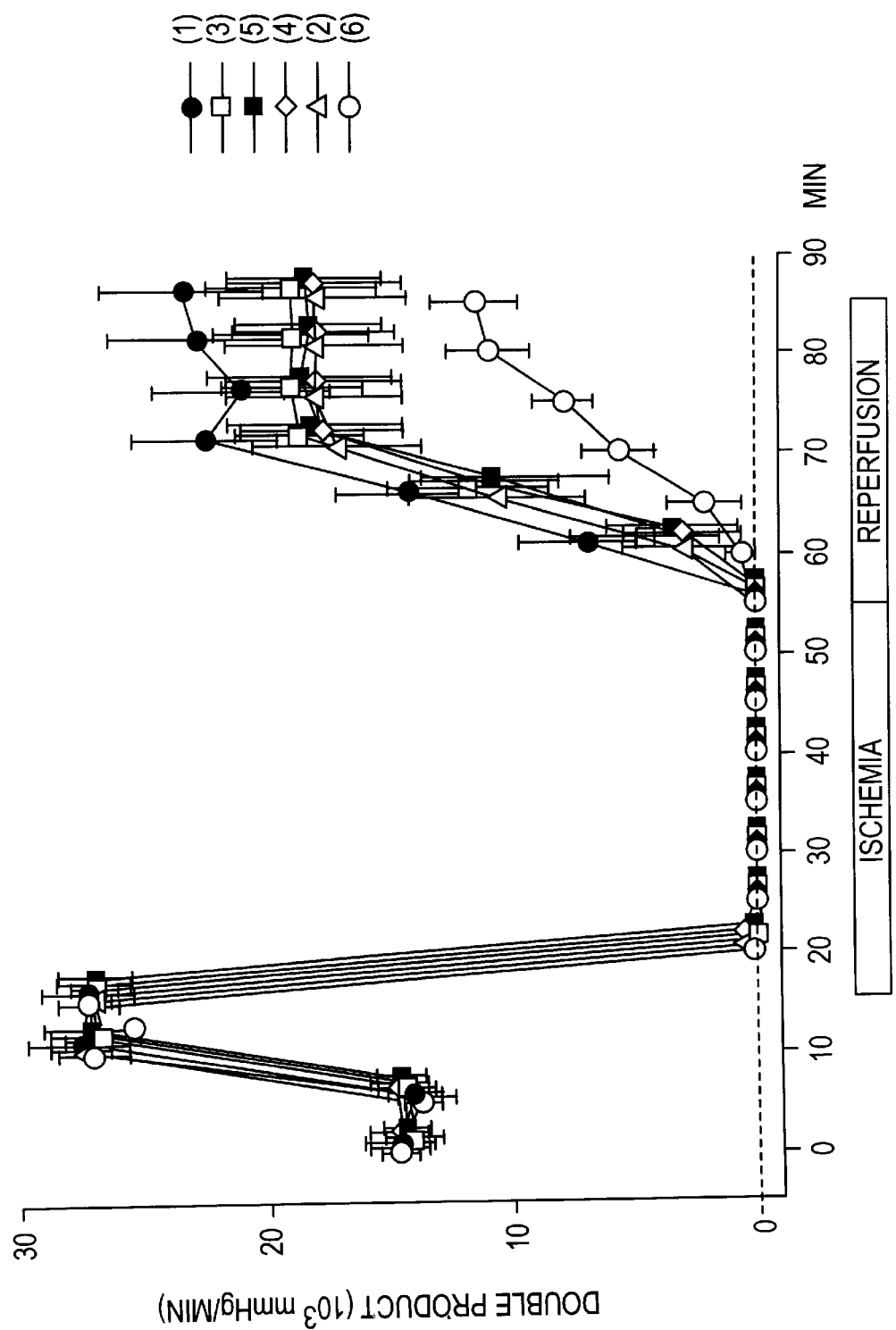
FIG. 2 is a graph showing the cardiac function restorative effect of the drug of this invention as assayed in Test Example 2 presented hereinafter.

The results are shown in FIG. 2. In FIG. 2, the abscissa represents time (min.) and the ordinate represents double product ($\times 10^3$ mmHg/min.). Moreover, (1) represents the group treated with the drug obtained in Example 1 of this invention (Group 1), (2) represents the group treated with the drug prepared in Example 2 (Group 2), (3) represents the group treated with the drug obtained in Example 3 (Group 3), (4) represents the group treated with the drug obtained in Example 5 (Group 4), (5) represents the group treated with the drug obtained in Example 6 (Group 5), and (6) represents the control group treated with the perfusion fluid not containing any drug of the invention (Group 6).

It is apparent from FIG. 2 that in the restorative effect on cardiac function in the rat ischemia-reperfusion model by the working heart technique, the groups treated with the drugs of this invention ((1)–(5) in the graph) showed significantly favorable results as compared with the control group (Group 6, (6)) in which the perfusion fluid alone was used.

The above results suggest that the drug of this invention is very useful for the restoration of cardiac function following ischemia-reperfusion, contributing greatly to improved prognosis in the treatment of myocardial infarction.

Test Example 3

Adult mongrel dogs (body weight 7–20 kg) were intravenously dosed with 30 mg/kg of pentobarbital sodium and after institution of artificial respiration, the operation site was clipped of hairs and the femoral vein and femoral artery were cannulated for administration of the test drug and measurement of blood pressure, respectively.

Next, left thoracotomy was performed and the pericardium was incised to expose the left ventricle. Then, the left coronary artery was ablated. A silk suture for obstruction was passed on the coronary artery and the probe of an electromagnetic flow meter for blood pressure measurement was set in position. To determine the change in ventricular wall length, a pair of ultrasonic crystal probes were securely installed and an indwelling needle for measurement of left ventricular pressure was set in position.

As drugs, the cardiac rehabilitation agent according to Example 4 of this invention (Experimental Group) and, for comparison's sake, a comparison drug of the following formulation (Comparison Group) were respectively infused by means of a syringe pump (Terumo Corporation STC-525) at a rate of 0.1 ml/kg/min. For each group, a control group treated with physiological saline in lieu of the active drug was provided. <Formulation of the Comparison Drug>

Cytidine 30 mM+uridine 22.5 mM+thymidine 7.5 mM (molar ratio=4:3:1)

Beginning 10 minutes before initiation of the above administration by infusion, ECG, blood pressure, heart rate, intracardiac pressure, intraventricular muscle length and other hemodynamic parameters were recorded at 5-minute intervals. Moreover, 30 minutes after initiation of infusion, coronary artery obstruction was performed and, after 50 minutes, was released.

The above-mentioned hemodynamic parameters were measured over a period of 80 minutes after the beginning of infusion and the % change in intraventricular muscle length (% SS: segment shortening) was calculated in the same manner as in Test Example 1.

The number of cases was not less than 5 animals for each of the experimental and comparison groups and Tukey's test and Dunnett's test were used to test the statistical significance of measured values.

Figure 3:
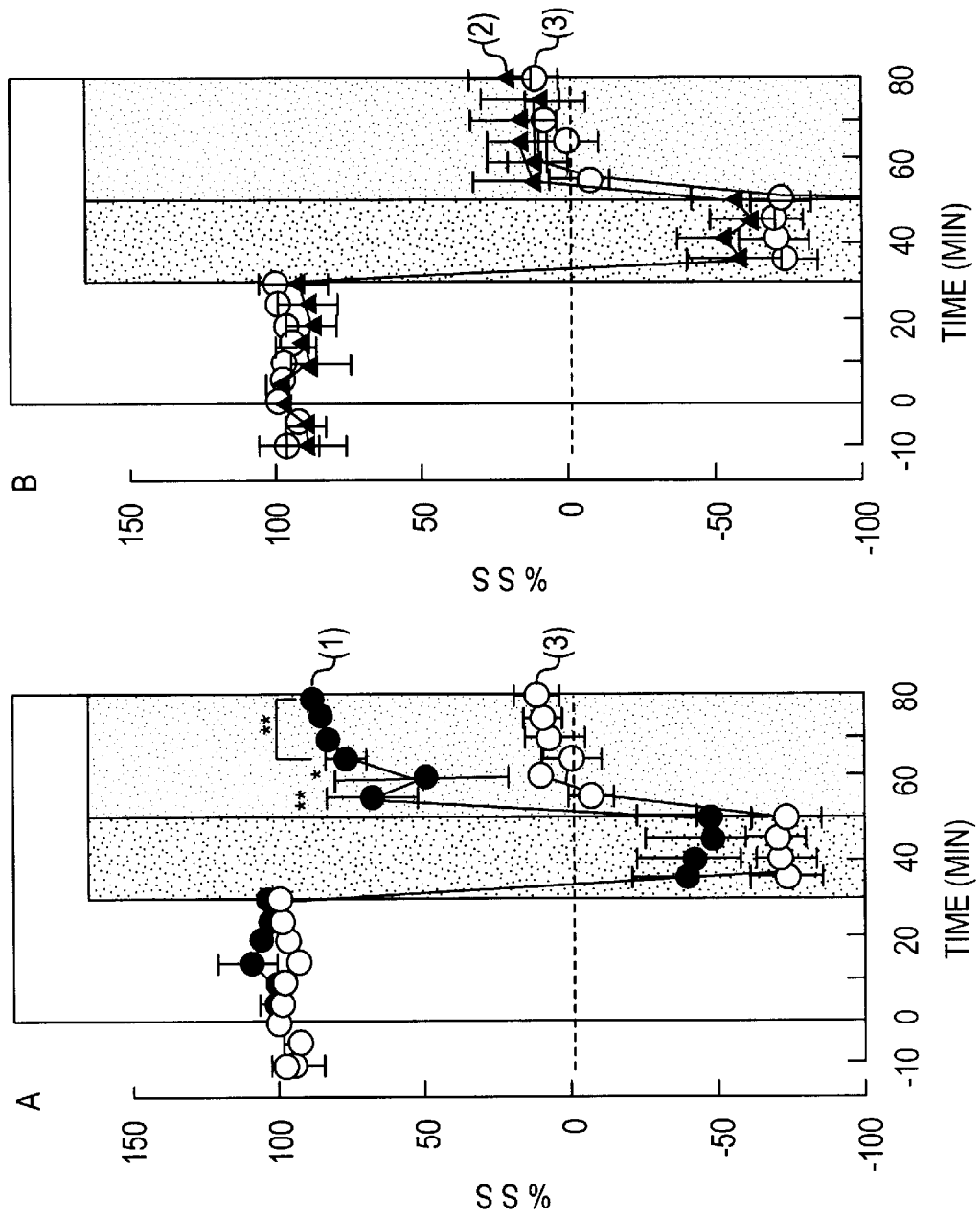
FIGS. 3A and 3B are graph showing the post-reperfusion myocardial contractility improving action of the drug of this invention as assayed in Test Example 3 presented hereinafter.

The results are shown, in the same fashion as FIG. 1, in FIGS. 3A and 3B (abscissa=time (min.), ordinate=% SS).

In the graphs, (1) represents the experimental group (Invention Group, n=5), (2) represents the comparison group (n=5), and (3) represents a control group (treated with saline, n=12). The segment 0–80 min. of the abscissa of each graph represents the period during which the test drug was administered by infusion, the segment 30–50 min. represents the period of ischemia, and the segment 50–80 min. represents the reperfusion period.

It is clear from FIG. 3A, too, that, in this model of acute myocardial infarction, post-reperfusion % SS is considerably improved in the group treated with the drug of this invention (Experimental Group) as compared with the saline control group, suggesting that the drug of this invention is capable of controlling stunning myocardium after ischemia-reperfusion without inducing any adverse reaction. It is, therefore, clear that the drug is very effective in the restoration of cardiac function following mechanical revascularization in the treatment of myocardial infarction, contributing a great deal to improved prognosis. In contrast, as shown in FIG. 3B, the remarkable cardiac function-restoring effect of this invention could not be obtained in the comparison group treated with nucleic acid components other than the purine nucleosides and purine nucleotides used as active components of this invention, even though they also are nucleic acid components.

INDUSTRIAL APPLICABILITY

In accordance with this invention there is provided a novel cardiac rehabilitation agent which prevents or palliates myocardial contraction disturbance to maintain cardiac function in good order and is not accompanied by side effects which might adversely affect myocardial metabolism. This drug is capable of producing excellent responses for the restoration of cardiac function after mechanical revascularization, particularly in myocardial infarction.

We claim:

1. A method of restoring cardiac function following ischemia-reperfusion comprising administering to a subject in need thereof a pharmaceutically effective amount of a cardiac rehabilitation composition consisting essentially of:
   (i) at least one purine nucleoside, with the proviso that the purine nucleoside is not adenosine, and
   (ii) at least one purine nucleotide or salt thereof; or
   (i) at least one purine nucleoside, with the proviso that the purine nucleoside is not adenosine, and
   (ii) at least one purine nucleotide or salt thereof and
   (iii) at least one pyrimidine nucleoside.

2. The method according to claim 1, wherein said purine nucleoside is inosine.

3. The method according to claim 1, wherein said purine nucleotide is guanosine 5'-monophosphate.

4. The method according to claim 1, wherein at least one purine nucleoside is inosine and at least one purine nucleotide is guanosine 5'-monophosphate.

5. The method according to claim 1, wherein cytidine and uridine are used in combination as said pyrimidine nucleosides.

6. A method of restoring cardiac function following ischemia-reperfusion comprising administering to a subject in need thereof a pharmaceutically effective amount of a cardiac rehabilitation composition consisting essentially of inosine, cytidine, uridine, guanosine 5'-monophosphate or salt thereof, and thymidine.

7. The method according to claim 6, wherein said composition consists essentially of inosine, cytidine, uridine, a salt of guanosine 5'-monophosphate, and thymidine in a molar ratio of 4:4:3:4:1.

8. The method according to claim 1, wherein at least one purine nucleoside is inosine, at least one purine nucleotide is guanosine 5'-monophosphate and at least one pyrimidine nucleoside is two pyrimidine nucleosides, two pyrimidine nucleosides being cytidine and uridine.

* * * * *